United States Patent [19]

Erickson et al.

[11] Patent Number: 5,184,629
[45] Date of Patent: Feb. 9, 1993

[54] MALE URINARY ANTI-INCONTINENCE DEVICE AND METHOD

[75] Inventors: Richard A. Erickson, St. Paul; Gerald W. Timm, Deephaven, both of Minn.

[73] Assignee: Dacomed Corporation, Minneapolis, Minn.

[21] Appl. No.: 692,818

[22] Filed: Apr. 25, 1991

Related U.S. Application Data

[63] Continuation of Ser. No. 325,599, Mar. 20, 1989, abandoned.

[51] Int. Cl.⁵ ............................ A61F 5/48; A61F 2/00
[52] U.S. Cl. ........................................ 128/885; 600/29
[58] Field of Search ................. 606/151, 157; 128/79,
128/DIG. 25, 885, 869, 87 A, 87 R, 88, 842,
844, 918; 251/4, 9, 10; 24/306, 442, 487;
600/29-31

[56] References Cited

U.S. PATENT DOCUMENTS

| | | | |
|---|---|---|---|
| 678,943 | 7/1901 | Davis | 606/157 |
| 1,133,958 | 3/1915 | Henderson | 128/79 |
| 1,728,322 | 9/1929 | Badrian | 606/157 |
| 1,748,227 | 2/1930 | Hyams | 606/157 |
| 1,750,654 | 3/1930 | Wappler | 606/157 |
| 2,533,924 | 12/1950 | Foley | 128/885 |
| 2,618,270 | 11/1952 | Pearson, Jr. | 128/885 |
| 2,756,753 | 7/1956 | Means | 128/DIG. 25 |
| 3,147,754 | 9/1964 | Koessler | 128/79 |
| 3,155,096 | 11/1964 | Outwin | 128/885 |
| 3,203,421 | 8/1965 | Bialick | 128/885 |
| 3,866,611 | 2/1975 | Baumrucker | 128/DIG. 25 |
| 4,102,342 | 7/1978 | Akiyama et al. | 606/192 |
| 4,534,353 | 8/1985 | de Leur | 606/157 |
| 4,800,900 | 1/1989 | French | 128/885 |

FOREIGN PATENT DOCUMENTS

| | | | |
|---|---|---|---|
| 0197810 | 10/1978 | Fed. Rep. of Germany | 128/DIG. 25 |
| 8804542 | 6/1988 | World Int. Prop. O. | 128/88 |

OTHER PUBLICATIONS

Two-Page VOLTEX TM Product Sheet, VOLTEK, Division of Sekisui America Corporation (Exhibit A).
Two-Page Product Sheet on the "COOK ® Continence Cuff" (Exhibit B).
One-Page Sheet on "Bard ® Cunningham Clamp", BARD Home Health Division, Berkeley Heights, N.J., Apr. 1980 (Exhibit C).
One-Page Sheet on "Baumrucker Urinary Incontinence Clamp", Greenwald Surgical Company, Inc., Lake Station, Ind. (Exhibit D).
Two-Page Product Sheet on PENORING Clamp, Koken Company, Ltd., Tokyo, Japan (Exhibit E).
Three-Page Article Entitled, "Urinary Incontinence: Control by External Device", reprint from *Archives of Physical Medicine and Rehabilitation*, vol. 54, Aug., 1973, Copyright, 1973, American Congress of Rehabilitation Medicine, authors: William E. Bradley, M.D., Gerald W. Timm, Ph.D., and F. Brantley Scott, M.D. (Exhibit F).
Article entitled, "An External Device for Management of Male Urinary Incontinence", by Paul Citron, Gerald W. Timm and William E. Bradley, reprint from *J. Biomechanics*, pp. 257-260, 1972, vol. 5 (Exhibit G).

*Primary Examiner*—Michael A. Brown
*Attorney, Agent, or Firm*—Merchant, Gould, Smith, Edell, Welter & Schmidt

[57] ABSTRACT

An external male anti-incontinence device (20) including a cradle member (22) and elastic strap assembly (24). The cradle member (22) includes a dorsal arm member (26) and a ventral arm member (28) in axial alignment with an opening (29) defined intermediate thereof. The ventral arm member (28) includes an integral urethral occlusion pad (30). The cradle member (20) includes integral hinges (32) interconnecting the dorsal and ventral arm members (26, 28). The cradle member (22) being hinged about an axis perpendicular to the axial alignment of dorsal and ventral arm members (26, 28) such that when positioned onto a penile shaft (60) the cradle member (22) is hinged about an axis perpendicular to the axis of the penile shaft (60).

13 Claims, 3 Drawing Sheets

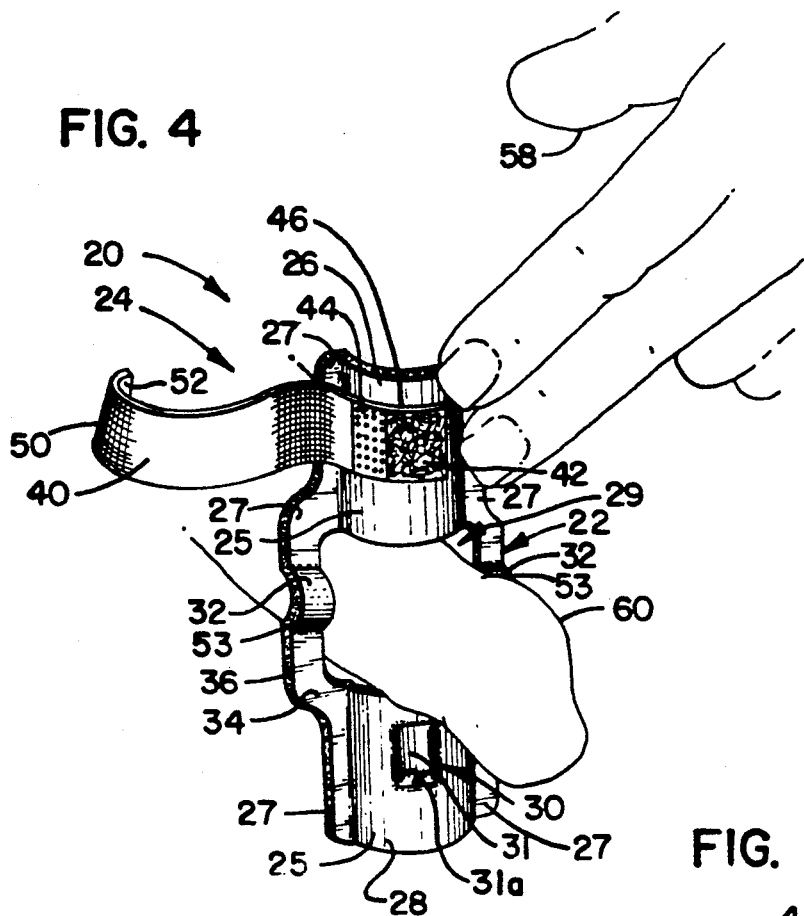
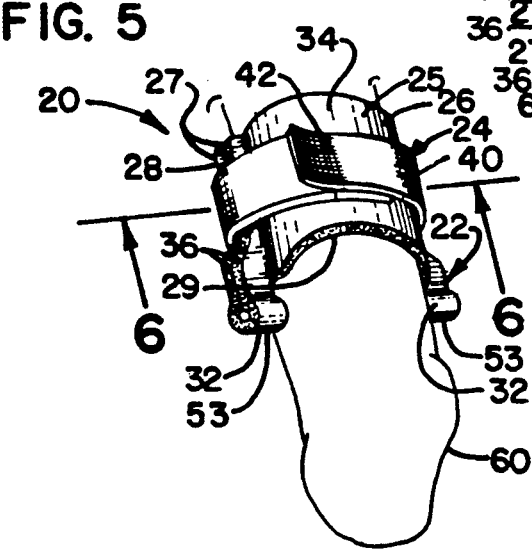

MALE URINARY ANTI-INCONTINENCE DEVICE AND METHOD

This is a continuation of application Ser. No. 07/325,599, filed Mar. 20, 1989, which was abandoned upon the filing hereof.

TECHNICAL FIELD OF THE INVENTION

The present invention relates to an external male urinary anti-incontinence device and method. In particular the invention relates to a device and method for preventing the involuntary leakage of urine in incontinent males by applying sufficient pressure to occlude the urethra along the ventral penile shaft.

BACKGROUND OF THE INVENTION

There are many types of devices and methods for treating male urinary incontinence using external penile appliances. A spring loaded, external penile device is discussed in two articles: See *Urinary Incontinence: Control by External Device*, Archives of Physical Medicine and Rehabilitation, August, 1973, Vol. 54, pp. 376-378 and *An External Device for Management of Male Urinary Incontinence*, J. Biomechanics, 1972, Vol. 5, pp. 257-260.

At least four such devices are currently being marketed: 1) Cunningham Clamp—Bard Home Health Care Division, C. R. Bard, Inc., Berkley Heights, N.J. 07922; 2) Baumrucker Clamp—Greenwald Surgical Co., Inc., 2688 DeKalb St., Lake Station, Ind. 46405; 3) Penoring Clamp—Koken Co., Ltd., Tokyo, Japan; and 4) Cook Continence Cuff—VPI, A Cook Group Company, 127 South Main Street, Spencer, Ind. 47460.

Known U.S. patents are U.S. Pat. Nos. 4,102,342; 3,866,611; 3,203,421; 3,155,096; 3,147,754; 2,756,753; 2,618,270; 2,533,924; and 1,728,322.

There are several disadvantages associated with many existing devices and methods for treating male urinary incontinence using an external penile appliance. One typical problem is that these devices often tend to restrict the blood supply to the penile shaft which can cause discomfort to the user and in extreme cases can result in tissue necrosis. This is due in part because many of these devices restrict the penile shaft between two relatively flat, narrow, and rigid members.

Yet another problem with many existing devices is that they orient the hinge axis parallel to the axis of the penile shaft. This often results in uneven pressure zones on the penile shaft. In particular, devices with a parallel hinge axis orientation typically apply pressure on the tissue positioned closest to the hinge.

Yet another problem with many existing devices is they are sensitive to tension adjustment such that the tension affects the force applied by the device to the penile shaft. Thus it is possible for the user to inadvertently tighten the device too much such that the blood supply to the penis is restricted.

Many existing devices are bulky and difficult for the user to conceal. Snaps, hooks, buckles, nonelastic tape, etc. which are used to attach the devices to the penile shaft are often uncomfortable and a source of irritation.

Additionally, the cost of existing devices is often too expensive to be disposable after a period of use or when becoming soiled. Failure to replace these devices because of soiling can result in reduced personal hygiene and patient safety.

The present invention solves these and other problems associated with the prior art.

SUMMARY OF THE INVENTION

The present invention relates to an external male anti-incontinence device including a cradle member having a dorsal arm member with a curvilinear surface and a ventral arm member with a curvilinear surface. The dorsal and ventral arm members are in axial alignment with each other with an aperture being defined intermediate of the dorsal and ventral arm members. The ventral arm member includes a pressure pad integral therewith. The cradle member includes integral hinges interconnecting the dorsal and ventral arm members, the cradle member being hinged about an axis perpendicular to the axial alignment of the dorsal and ventral arm members whereby the cradle member can be folded over into a folded state so that the curvilinear surfaces of the dorsal and ventral arm members are facing one another with the pressure pad projecting into a cavity formed between the facing curvilinear surfaces of the dorsal and ventral arm members. A strap assembly is used for releasably retaining the cradle member in the folded state.

The external male anti-incontinence device of the present invention incorporates a curvature in the dorsal and ventral arm members which conforms to the cylindrical contour of the penile shaft. This causes the force applied to the penile shaft by the invention to be applied radially and eliminates localized areas of constricted blood flow in the penile shaft. The dorsal and ventral arm members are sized and configured such that although the forces applied by the pressure pad, also referred to as occlusion pad, are sufficient to prevent urine leakage through the urethra, the overall pressure applied to the penile shaft is reduced due in part to the increased contact area of the dorsal and ventral arm members on the penile shaft.

The present invention has a hinge axis which is perpendicular to the penile shaft axis and to the axial alignment of the dorsal and ventral arm members which assists in alignment of the dorsal and ventral arm members and prevents the occurrence of any uneven pressure zones on the penile shaft.

A preferred embodiment of the present invention inherently limits the amount of pressure that can be applied to the penile shaft and provides the flexibility to accommodate changes in penile shaft size while wearing the device. This ability to accommodate changes in penile shaft size is due in large part to the use of an elastic strap assembly which attaches the device to the penile shaft.

In the preferred embodiment, the integral urethral occlusion pad (pressure pad) of the device limits the pressure applied to the urethra to a specific amount above the pressure applied to the penile shaft by the ventral and dorsal arm members. This is accomplished by limiting the extent that the occlusion pad protrudes from the concave surface of the ventral arm member. Additionally, this feature reduces the possibility of restricting the blood supply to the penile shaft and decreases the significance of tension in the strap assembly so as to assure proper attachment of the device to the penile shaft.

A preferred embodiment of the present invention includes flanges along the periphery of the dorsal and ventral arm members which prevent closure of the device beyond contact between the flanges. This limits the maximum force that can be applied to the penile shaft and the urethra.

An advantage of a preferred embodiment of the present invention is that the cradle member with its dorsal and ventral arm members, hinges, and pressure pad is made of a one-piece construction so as to reduce the manufacturing costs such that the device can be disposed of and replaced after a period of use or when the device has become soiled, thereby resulting in improved personal hygiene and patient safety.

Yet another advantage of a preferred embodiment of the present invention is that it is more compact and concealable than existing devices.

A preferred embodiment of the present invention is fabricated from a composite material made up of a semi-rigid polyolefin surface coating fused to closed cell, chemically cross-linked polyethylene foam. In the preferred embodiment, the composite material is thermoformed to the desired contour and then die cut to the correct external dimensions. In the preferred embodiment, the present invention is sufficiently sized to generally retain its shape and yet have some give and flexibility.

Another advantage of a preferred embodiment of the present invention is that it uses an elastic strap which increases user comfort and allows for variable separation of the dorsal and ventral arm members as the penile shaft increases and decreases in diameter.

These and various other advantages and features of novelty which characterize the invention are pointed out with particularity in the claims annexed hereto and forming a part hereof. However, for a better understanding of the invention, its advantages, and the objects obtained by its use, reference should be made to the accompanying drawings and descriptive matter, which form a further part hereof, and in which there is illustrated and described a preferred embodiment of the invention.

BRIEF DESCRIPTION OF THE DRAWINGS

In the drawings wherein like reference numerals generally indicate corresponding parts throughout the several views;

FIG. 4 is a perspective view illustrating placement of the device shown in FIG. 1 onto a penis;

FIG. 5 is a perspective view illustrating the device shown in FIG. 1 in its folded, operative state on the penis;

FIG. 6 is a sectional view as generally seen along line 6—6 in FIG. 5 illustrating minimal spacing between the dorsal and ventral arm members;

DETAILED DESCRIPTION OF A PREFERRED EMBODIMENT OF THE PRESENT INVENTION

Figure 1:
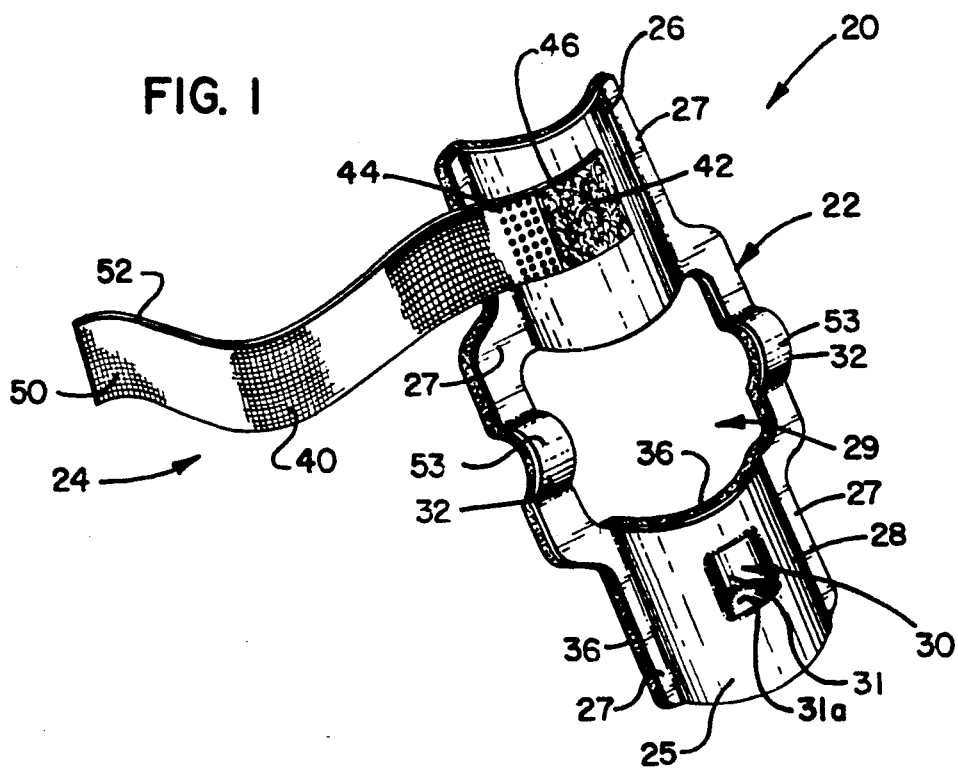
FIG. 1 is a perspective view of a preferred embodiment of an external male anti-incontinence device in accordance with the principles of the present invention.
Figure 3:
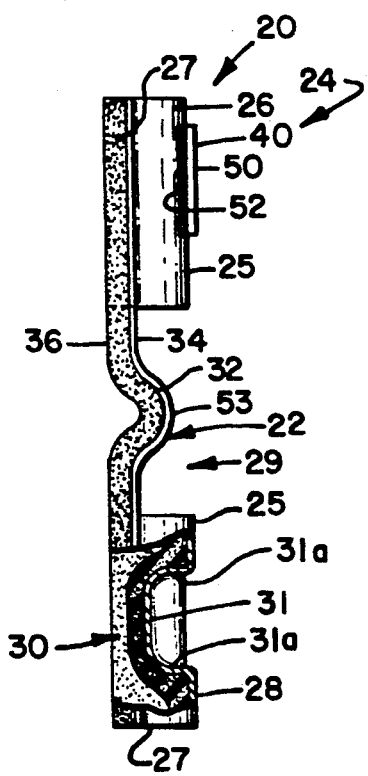
FIG. 3 is a sectional view as generally seen along line 3—3 in FIG. 2.
Figure 2:
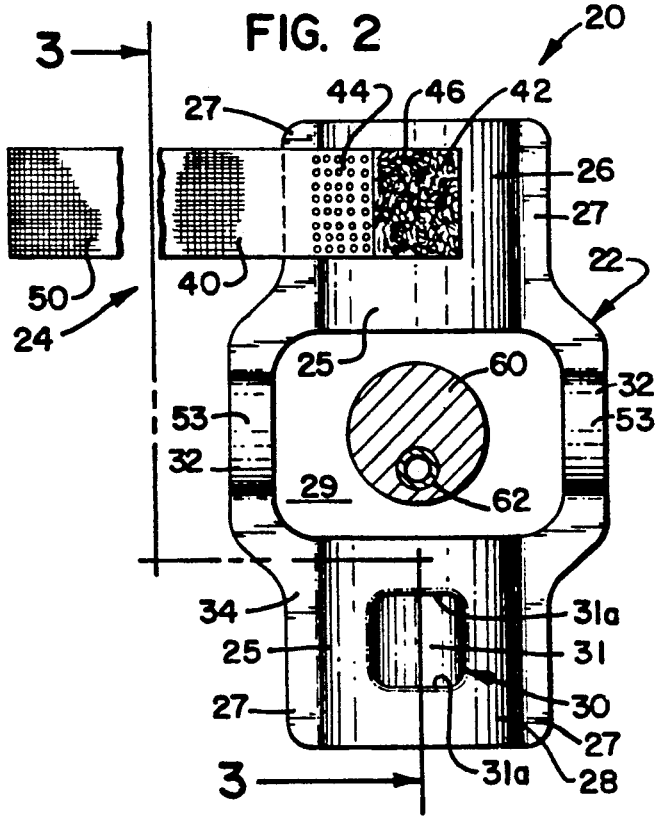
FIG. 2 is a planar view of the embodiment shown in FIG. 1.

Referring now to the figures, there is illustrated a preferred embodiment of an external male anti-incontinence device in accordance with the principles of the present invention, the device being referred to by the reference numeral 20. The device 20 includes a one-piece cradle member 22 and a strap assembly 24. The cradle member 22 includes a dorsal arm member 26 and a ventral arm member 28 in axial alignment with each other. The dorsal and ventral arm members 26, 28 have a curvilinear surface 25 with axially extending flanges 27 extending along the sides thereof. An aperture 29, sized to receive a penile shaft, is defined intermediate of the dorsal and ventral arm members 26, 28. The ventral arm member 28 includes integral therewith a urethral occlusion pad 30, also referred to as a pressure pad, having a bottom wall portion 31 and curvilinear side wall portions 312. The cradle member 22 includes integral hinges 32 interconnecting the dorsal and ventral arm members 26, 28. The cradle member 22 is hinged about an axis perpendicular to the axial alignment of the dorsal and ventral arm members 26, 28 and to the longitudinal axis of the penile shaft when positioned thereon.

The cradle member 22 has a semi-rigid plastic coating layer 34 and a soft foam layer 36. The plastic layer 34 is disposed on convex side of the curvilinear surfaces 25 with the foam layer 36 disposed on a concave side of the curvilinear surfaces 25. In the preferred embodiment the cradle member 22 is fabricated from VOLEX (a U.S. registered trademark) extrusion coated composite made up of polyolefin surface coatings fused to closed-cell, chemically cross-linked polyethylene foam. VOLEX is available from Voltek, a Division of Sekisui America Corp., 100 Shepard Street, Lawrence, Mass. 01843. The material is thermoformed to the desired contour and then die cut to the correct external dimensions. Different sizes of the cradle member 22 are preferably made to fit different diameters of penile shafts.

The cradle member 22 can also be constructed using alternative materials and known fabrication techniques. Examples include, but are not limited to, thermoformed polystyrene with separately attached foam padding and injection molded or extruded plastics and/or nonplastics with separately attached or integral foam padding.

In the preferred embodiment shown, the strap assembly 24 includes an elastic strap 40 having an elastic backing 50 and a loop material 52. The elastic strap 40 is attached to a strap 42 proximate an end portion 44 by ultrasonic welding. The strap 42 is attached to the convex side of the dorsal arm member 26 by a pressure sensitive adhesive layer 46. The strap 42 includes hook material for releasable attachment to the loop material 52 of the elastic strap 40. In one embodiment of the present invention, the elastic strap 40 is a length of VEL-STRETCH (registered U.S. trademark) elasticized loop tape and the strap 42 is VELCRO (registered U.S. trademark) hook tape. The elasticized loop tape is ultrasonically welded to the hook tape in a back strap configuration. The elastic strap 40 accommodates changes in penile shaft size by allowing the dorsal and ventral arm members 26, 28 to move apart from one another as the penile shaft size increases. Then when the penile shaft size decreases, the elastic strap 40 pulls the dorsal and ventral arm members 26, 28 back toward each other.

The strap assembly can also be constructed using alternative materials including, but not limited to, nonelastic loop tape, elastic webbing, foam tape, and plastic or cloth materials. Closure methods could include, but are not limited to, snaps, hooks, buckles, and pressure sensitive adhesives.

In the preferred embodiment shown, the integral hinges 32 are formed in the cradle member 22 by raised arches 53 where the hinge action is to occur. The hinges are preferably formed when thermoforming the surface coating 34 and its associated foam layer 36 to the desired contour.

Referring now to FIGS. 4-6, the external male anti-incontinence device 20 is illustrated in FIG. 4 while being positioned onto a penile shaft 60 and is illustrated in FIG. 5 in its folded, operative state on the penile shaft 60. In use, the user grasps the cradle member 22 with his hand(s) 58 and inserts the penile shaft 60 through the opening 29 with the concave side of the dorsal and ventral arm members facing toward the user's body. The device 22 is positioned at the base of the penile shaft 60 and folded so the dorsal arm member 26 is in contact with the dorsal side of the penile shaft 60 and the ventral arm member 28 is in contact with the ventral side of the penile shaft 60. The elastic strap 40 of the strap assembly 24 is then wrapped around the ventral arm member 28 and attached to the strap 42 on the dorsal arm member 26. The elastic strap 40 is place under sufficient tension to retain the device 20 securely in place on the penile shaft 60. The flanges 27 of dorsal and ventral arm members 26, 28 are separated from one another when the cradle member 22 is positioned in the penile shaft 60 in its folded state.

As illustrated in FIG. 6, when the device is in the folded, operative state on the penile shaft 60, the urethral occlusion pad 30 projects into a cavity 61 receiving the penile shaft 60 so as to be positioned adjacent to the urethra 62 and imparts sufficient force to block the urethra so as to prevent involuntary loss of urine.

To urinate or remove the device 20, the elastic strap 40 is released from the tape 42 on the dorsal arm member 26 thereby enabling the cradle member 22 to be unfolded and slipped of the penile shaft 60.

Figure 7:
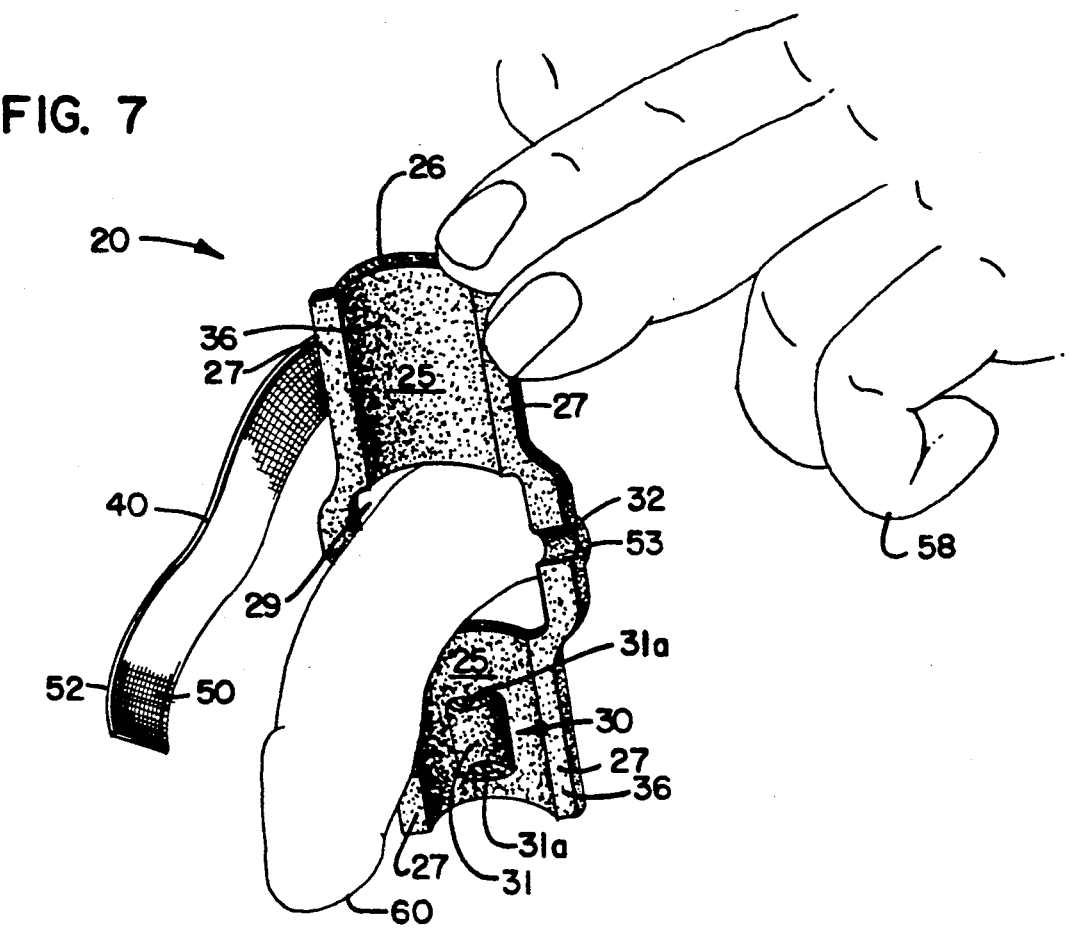
FIG. 7 is a view similar to FIG. 4 illustrating an alternative method of placing the device onto a penis such that concave surfaces of the device face away from the user.
Figure 8:
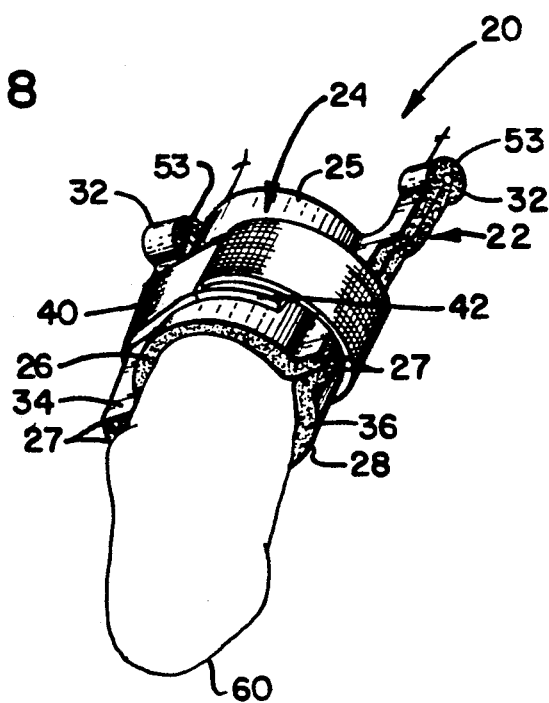
FIG. 8 is a view similar to FIG. 5 showing the device in its folded, operative state after being inserted onto the penis according to the method shown in FIG. 7.

FIGS. 7 and 8 illustrate and alternative method of positioning the device 20 on the penile shaft 60. In this method, the device 20 is inserted onto the penile shaft 60 with the concave side of the dorsal and ventral arm members 26, 28 facing away from the user's body as generally illustrated in FIG. 7. The cradle member 22 is then folded into its operative position as illustrated in FIG. 8 with the hinges 32 being adjacent the base of the penile shaft 60 and the dorsal and ventral arm members 26, 28 extending away toward a distal end of the penile shaft 60.

It is to be understood, that even though numerous characteristics and advantages of the invention have been set forth in the foregoing description, together with details of the structure and function of the invention, the disclosure is illustrative only, and changes may be made in detail, especially in matters of shape, size, and arrangement of the parts within the principles of the invention to the full extent indicated by the broad general meaning of the terms in which the appended claims are expressed.

What is claimed is:

1. An external male anti-incontinence device, comprising:

a) a cradle member including a dorsal arm member having a curvilinear surface and a ventral arm member having a curvilinear surface, the dorsal and ventral arm members being in axial alignment with each other, an aperture being defined intermediate of the dorsal and ventral arm members, the ventral arm member including an integral pressure pad, the cradle member further including integral hinges interconnecting the dorsal and ventral arm members, the cradle member being hinged about an axis perpendicular to the axial alignment of the dorsal and ventral arm members whereby the cradle member can be folded over into a folded state so that the curvilinear surfaces of the dorsal and ventral arm members are facing one another with the pressure pad projecting from the ventral arm member into a cavity formed between the facing curvilinear surfaces of the dorsal and ventral arm members, said pressure pad having a substantially smaller surface area than the inner surface area of the ventral arm member to block urine leakage through the urethra; and b) strap assembly means for releasably retaining the cradle member in the folded state.

2. A device according to claim 1, wherein the strap assembly includes a length of elasticized tape attached to the cradle member proximate one end and including a loop material releasably attachable to hook material attached to the cradle member.

3. A device according to claim 1, wherein the cradle member comprises a polyolefin surface coating fused to closed-cell, chemically cross-linked polyethylene foam.

4. A device according to claim 3, wherein the cradle member is thermoformed.

5. A device according to claim 1, wherein the cradle member includes a top semi-rigid plastic layer attached to a bottom foam layer.

6. A device according to claim 1, wherein the dorsal and ventral arm members include flange means along their edges for limiting the force applied by the dorsal and ventral arm members.

7. A device according to claim 6, wherein the strap assembly includes an elastic member retaining the dorsal and ventral arm members in the folded state, the elastic member enabling variable separation of the dorsal and ventral arm members.

8. A device according to claim 1, wherein the hinges are formed as arches in the cradle member.

9. A device according to claim 1, wherein the cradle member is made of a one-piece construction.

10. A method for controlling male urinary incontinence using an external penile device having an opening for receipt of a penile shaft, dorsal and ventral arm members, and a urethral occlusion pad, the method comprising the steps of:

a) inserting the device onto the penile shaft;
    b) hinging the device into a folded, operative state about an axis perpendicular to the penile shaft so that the urethral occlusion pad is blocking the urethra; and
    c) releasably attaching the device onto the penile shaft by use of an elastic strap assembly.

11. An external male anti-incontinence device, comprising:

a) cradle means for positioning on a penile shaft, the cradle means including a dorsal arm member and a ventral arm member in axial alignment with one another generally along a longitudinal axis of the cradle means, the cradle means including an aperture intermediate of the dorsal and ventral arm members, the cradle means being hinged about an axis perpendicular to the longitudinal axis of the cradle means so that the cradle means is foldable between an unfolded state and a folded state wherein the dorsal and ventral arm members are facing one another, the ventral arm member including a pressure pad projecting from the ventral arm member into a cavity formed between the facing dorsal and ventral arm members when in the folded state, said pressure pad having a substantially smaller surface area than the inner surface area of the ventral arm member to block urine leakage through the urethra; and b) means releasably connecting the dorsal and ventral arm members for retaining the cradle means in the folded state.

12. An external male anti-incontinence device, comprising:

a) a cradle member of one-piece construction including a dorsal arm member having a curvilinear surface and a ventral arm member having a curvilinear surface, the dorsal and ventral arm members being in axial alignment with each other, an aperture being defined intermediate of the dorsal and ventral arm members, the ventral arm member including an integral pressure pad, the cradle member further including integral hinges interconnecting the dorsal and ventral arm members, the cradle member being hinged about an axis perpendicular to the axial alignment of the dorsal and ventral arm members whereby the cradle member can be folded over into a folded state so that the curvilinear surfaces of the dorsal and ventral arm members are facing one another with the pressure pad projecting from the ventral arm member into a cavity formed between the facing curvilinear surfaces of the dorsal and ventral arm members, said pressure pad having a substantially smaller surface area than the inner surface area of the ventral arm member to block urine leakage through the urethra; and b) strap assembly means for releasably retaining the cradle member in the folded state.

13. An external male anti-incontinence device, comprising:

a) cradle means for positioning on a penile shaft, the cradle means including a dorsal arm member and a ventral arm member in axial alignment with one another generally along a longitudinal axis of the cradle means, the cradle means including an aperture intermediate of the dorsal and ventral arm members, the ventral arm member including an integral pressure pad, the cradle means further including integral hinges interconnecting the dorsal and ventral arm members, the integral hinges being at least in part contoured and being further hinged about an axis perpendicular to the longitudinal axis of the cradle means so that the cradle means is foldable between an unfolded state and a folded state, said pressure pad having a substantially smaller surface area than the inner surface area of the ventral arm member to block urine leakage through the urethra; and b) means for releasably connecting the dorsal and ventral arm members for retaining the cradle means in the folded state.

* * * * *